United States Patent [19]
Harris

[11] Patent Number: 5,935,066
[45] Date of Patent: Aug. 10, 1999

[54] SYSTEM AND METHOD FOR MEASURING OF LUNG VASCULAR INJURY BY ULTRASONIC VELOCITY AND BLOOD IMPEDANCE

[75] Inventor: Thomas R. Harris, Nashville, Tenn.

[73] Assignee: Vanderbilt University, Nashville, Tenn.

[21] Appl. No.: 09/032,713

[22] Filed: Feb. 27, 1998

Related U.S. Application Data

[60] Provisional application No. 60/038,923, Feb. 27, 1997.

[51] Int. Cl.$^6$ ................................ A61B 8/00; A61B 5/05
[52] U.S. Cl. .......................... 600/436; 600/506; 600/547
[58] Field of Search .................................. 600/438, 371, 600/506, 547

[56] References Cited

U.S. PATENT DOCUMENTS

| | | | |
|---|---|---|---|
| 5,453,576 | 6/1995 | Krivitski | 128/668 |
| 5,595,182 | 6/1995 | Krivitski | 128/692 |
| 5,749,369 | 5/1998 | Rabinovich et al. | 600/547 |

OTHER PUBLICATIONS

Hunter, M. and Lee, J., Determination of Fluid Extraction and Osmotic Conductance sK in the Lung with Hypertonic NaCl Infusion I, Theory, Microsvasc. Res. 44:307–333, 1992.

Hunter, M. and Lee, J., Determination of Fluid Extraction and Osmotic Conductance sK in the Lung with Hypertonic NaCl Infusion II, Experiments, Microsvasc. Res. 44:307–333, 1992.

Krivitski, N.M., Novel Method to Measure Access Flow During Hemodialysis by Ultrasound Velocity Dilution Technique. ASIO J. 41: M741–M745, 1995.

*Primary Examiner*—Francis J. Jaworski
*Attorney, Agent, or Firm*—Waddey & Patterson; Mark J. Patterson

[57] ABSTRACT

The present invention is a method for assessing capillary permeability to determine vascular lung injury without requiring the injection of radioactive material or requiring the sampling of blood. The method includes measuring impedance and ultrasonic velocity of blood flow through a lung. A hypertonic bolus is injected into the blood flow, and measurements of the blood flow are taken to determine the ultrasonic velocity and the electrical impedance of the blood. These measurements are used to calculate the capillary transport quantity, which is the product of the reflection coefficient for movement of fluid across the capillary barrier and the filtration coefficient. The measured value of the capillary transport quantity can then be compared to a conventional capillary transport quantity for healthy lungs, and one can determine injury by a significant decrease in the measured capillary transport quantity as compared to the standard measurements.

Furthermore, a comparison of the osmotic transient graphs of the plotted indicator curves can serve to acknowledge lung vascular injury. Lung injury can be determined from the measured data when the point of osmotic equilibrium (where the indicator curve crosses the baseline) is significantly delayed as compared to the point of osmotic equilibrium plotted for a healthy lung.

6 Claims, 5 Drawing Sheets

SYSTEM AND METHOD FOR MEASURING OF LUNG VASCULAR INJURY BY ULTRASONIC VELOCITY AND BLOOD IMPEDANCE

This application claims priority to copending U.S. Provisional Patent Application Ser. No. 60/038,923 filed Feb. 27, 1997, entitled "Measurement of Lung Vascular Injury by Ultrasonic Velocity."

BACKGROUND OF THE INVENTION

The present invention relates generally to a method for detecting and measuring lung vascular injury, and, more particularly, to a method for assessing capillary permeability to determine vascular lung injury without requiring the injection of radioactive material or requiring the sampling of blood.

Acute Respiratory Distress Syndrome (ARDS) is a major problem in patients in intensive care units (ICU). While the syndrome appears to have many causes, most etiologies lead to capillary injury and increased permeability pulmonary edema. Interest in this problem has stimulated efforts to quantitatively evaluate capillary injury in the lungs and monitor the time course of this injury and the pulmonary edema which results from it. For example, it has been shown in a series of studies in ARDS patients that one variable which differentiates recovery from acute lung injury from continued deterioration of lung function is the magnitude of capillary permeability-surface area (PS) for tracer exchange as determined by radioisotope indicator dilution studies of the lungs. A less invasive method of monitoring capillary injury would be valuable in close management of fluid and oxygen therapies currently used for these patients. In addition, such a system would be an indicator and a monitor of the effectiveness of new therapies which are under development and are aimed at immunological protection and gene therapy of the lung endothelium.

Generally, three methods are used for measuring major lung vascular functions, principally defined as pulmonary blood flow, exchange surface area of extravascular and intravascular volumes in the lung, and lung vascular permeability. These methods are the gamma emitter scanning (GES) technique using labeled macromolecules and blood markers, positron emission tomography (PET), and indicator dilution (ID). While quite useful, GES and PET are equipment intensive, expensive and require injection of radioactive materials.

In contrast, the indicator dilution method provides very high time resolution with collection times on the order of 30 seconds for the measurement of exchange, flow and volumes in the lung. The conventional radioisotope method requires small radiation doses. Both gamma and beta labels may be used and thus a variety of materials are potential probes of endothelial function. The method has been shown to quantitatively measure extravascular lung water, microvascular PS, and parameters which characterize saturable uptake by the endothelium. Tracers exist which can correct for alterations in capillary surface area in the lung. Parameters derived from such indicator curves are altered by lung vascular damage in animal experiments. Studies can be performed in patients under intensive care and provide measures of microvascular function which alter with severity of respiratory distress. Some tracers can be used as nonradioactive markers, and when appropriate instrumentation is used, can provide rapid readings of pulmonary blood flow and extravascular water volume. Advances in optical methods have allowed the extension of this nonradioactive approach to the measurement of lung vascular PS. There are disadvantages, however. There is no spatial resolution and the computations depend on models of flow distribution. Tracers must be injected. Arterial blood must be sampled for lung applications. The kinetics of transport for larger molecules cannot be measured.

Another method related to indicator dilution is the osmotic transient method. Using radioisotopes, this technique has been applied to the lung in baseline conditions and to the heart. Conventionally, the method relied on maintenance of an isogravimetric lung, injections of radioisotopes, and constant infusions of fairly large amounts of hypertonic solutions. The method produced parameters related to the product of the reflection coefficient for movement of fluid across the capillary barrier and the filtration coefficient (σK). There was good evidence that the filtration measurement included both the interendothelial and transendothelial movement of interstitial fluid. It has further been shown that hypertonic fluid movement through the lung is a highly sensitive instrument for the measurement of fluid density and could be used to measure the interstitial volume supplying fluid for exchange and the σK product for endothelium. This method shows that highly sensitive instruments could allow smaller amounts of hypertonic fluid to be infused. The disadvantages of the method are that it relies on step infusions of saline and required withdrawal sampling of lung perfusate for density analysis.

While several methods for minimally invasive assessment of capillary permeability are promising, most require the injection of foreign trace materials and many require blood sampling. Further, although much work has been done investigating the osmotic transients in the lung and other organs, and a body of research on the acoustic and electrical impedance properties of biological tissue exists, no work synthesizing these bodies of knowledge exists and this technique has never been applied to an injured lung. Furthermore, no evidence of the ability of the method to identify changes in capillary transport after acute lung injury has been presented.

What is needed, then, is a method for assessing capillary permeability to determine vascular lung injury without requiring the injection of radioactive material and without requiring the sampling of blood.

SUMMARY OF THE INVENTION

An object of the present invention is to provide a method for assessing capillary permeability to determine vascular lung injury without requiring the injection of radioactive material or requiring the sampling of blood. The method includes measuring impedance and ultrasonic velocity of blood flow through a lung. A hypertonic bolus is injected into the blood flow and changes in sound velocity and blood impedance are observed with either a flow-through probe or a catheter. The measurements are used to provide data to generate an indicator curve for ultrasonic velocity and an indicator curve for impedance. These measurements creating the indicator curves are then used to calculate the capillary transport quantity of the tested lungs, and this value is then compared to capillary transport quantity established for a healthy lung to determine if vascular lung injury is present.

This method provides for the rapid and minimally invasive measurement of the integrity of the capillary barrier in the lungs. It relies on the determination of ultrasonic velocity in blood as a primary quantity which will measure water extracted from the lung tissue spaces during the passage of a hypertonic bolus of saline through the lung circulation. In addition to the basic physics of sound in biological fluids, this invention discloses the mathematical theory of capillary exchange and transport to interpret this measurement and compute the capillary transport quantity ($\sigma K$), which is the product of the filtration coefficient and reflection coefficient of the microvascular barrier.

DESCRIPTION OF THE PREFERRED EMBODIMENTS

Figure 1:
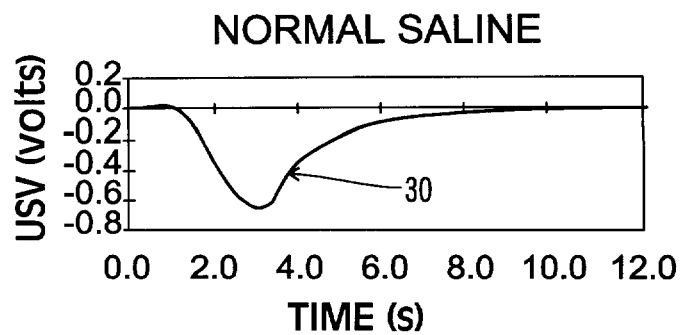
FIG. 1 is a graph of ultrasonic velocity versus time for flowing blood with a normal saline added.

The present invention is a method for assessing capillary permeability to determine vascular lung injury without requiring the injection of radioactive material. In a preferred embodiment of this invention, the measurements as described herein are taken using a flow-through (USV/Z) probe 10 (shown in FIG. 9). A second embodiment uses a special catheter tip 20 (shown in FIG. 10) that includes impedance sensors 26, 28 and sound velocity sensors 22, 24, the catheter tip 20 being inserted into a systemic arterial system. Both embodiments are used with a novel method in which the capillary transport quantity, which is the product of lung capillary reflection coefficient ($\sigma$) and capillary filtration capacity (K), is determined from sound velocity and blood impedance measurements are taken after the injection of a small bolus of hypertonic saline. Either embodiment can also provide measurements of interstitial lung water volume and cardiac output from the injection of a single bolus of hypertonic saline.

The quantity $\sigma K$ decreases with increased capillary permeability and lung vascular injury, and is an excellent indicator of lung capillary injury. Therefore, the system and method can be used to monitor pulmonary microcirculation and act as an early warning system for the onset of Acute Respiratory Distress Syndrome and increased permeability pulmonary edema. Sensors of the type disclosed in U.S. Pat. No. 5,453,576, issued to Transonic Systems, Inc. for an invention entitled "Cardiovascular measurements by sound velocity dilution" (incorporated by reference) can be used for this purpose.

The objective of the development of the method of this invention was to devise a mathematical model of the passage of an osmotic bolus (not shown) through the lung 51 (FIG. 11) and then perform experiments in isolated perfused lungs 51 under baseline conditions and observe injury by infusion of oleic acid into the blood perfusing the lung 51 to determine when lung injury has occurred.

Figure 11:
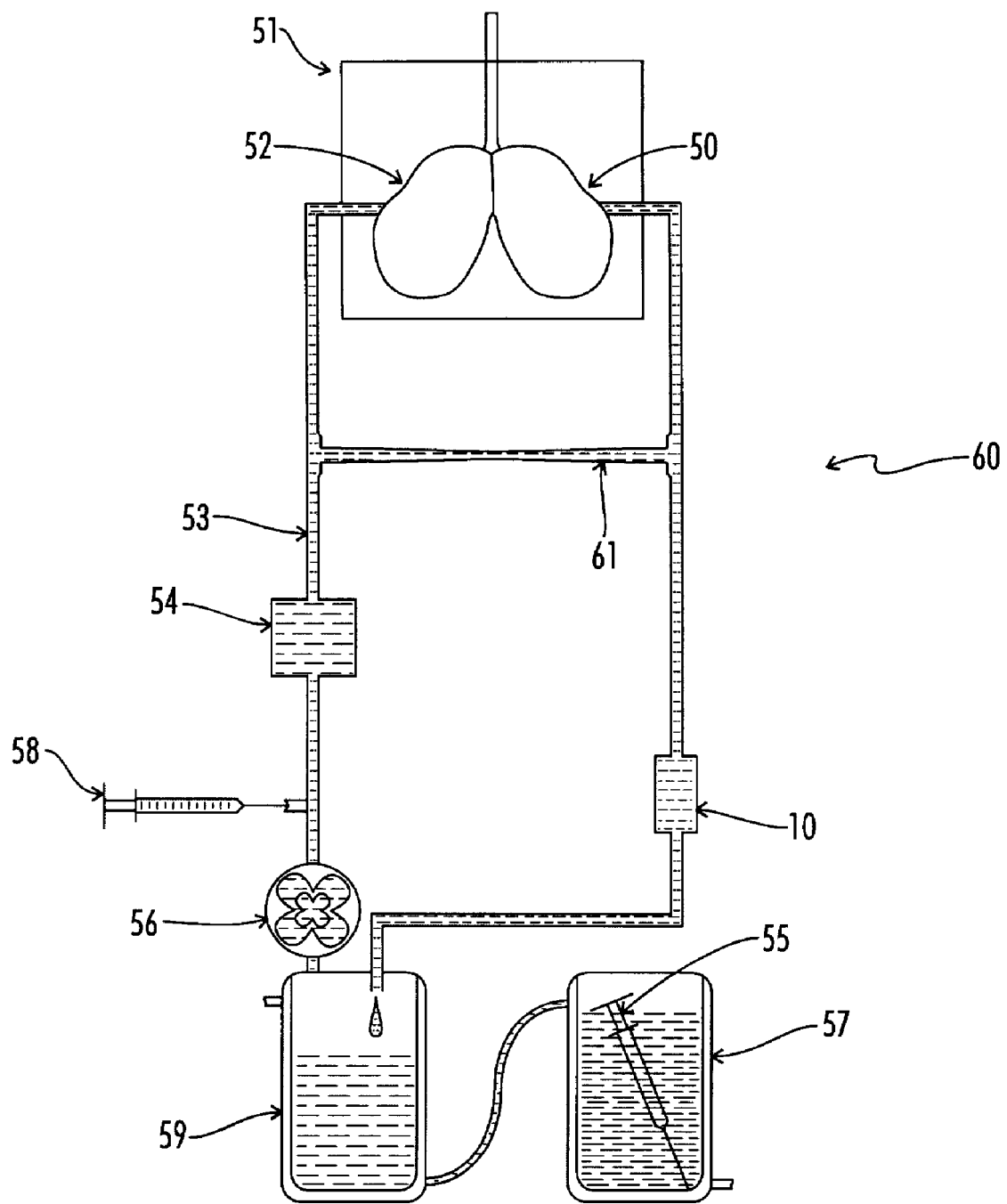
FIG. 11 is a schematic diagram of a ventilation and perfusion system including a blood reservoir, a pump, a mixing chamber, lungs extricated from an animal, and an ultrasonic velocity and impedance probe used to test and analyze the relationship between lung vascular injury and ultrasonic velocity and impedance of blood flow.

The research performed was on an arrangement of an isolated perfused dog lung system 60, illustrated in FIG. 11. The system 60 allows for circulation of blood through the lungs 51 of a mongrel dog (not shown) under uninjured and injured conditions so that measurements may be made of the ultrasonic velocity and electrical impedance of the blood. The lungs 51 were extricated from a dog (as discussed below), and arranged in the system 60 to have blood pumped through them. Blood flow in the system began with the pump 56. The blood is forced from the pump 56 to a mixing chamber 54, between which is an injection port 58 where the bolus is introduced into the blood circulation. The blood is then directed through the lungs 51, then through the USV/Z probe 10 for measurements of the ultrasonic velocity and electrical impedance of the blood. The blood is then collected in a blood reservoir 59 for recirculation through the system 60, further discussed below.

Five (5) mongrel dogs were anesthetized until no ocular reflex was evident. They were intubated and ventilated with an $O_2$-air mixture. The femoral artery and vein were catheterized with $\frac{1}{8}^{th}$ inch Tygon tubing. The dogs were exsanguinated via the arterial line and the blood was collected in a saline-flushed reservoir 59. A 500 mL volume of normal saline was administered via the venous line to increase blood volume. One to two liters of blood was obtained in this manner for each experiment. After a complete exsanguination, an incision was made between the fourth and fifth ribs of the dog through which the heart, lungs, and a section of the esophagus were removed. The apex portion of the left ventricle was resected, and a canula was fed through the ventricle into the left atrium where it was secured with cotton ligatures. A second canula was similarly secured in the right ventricle. The right lobe of the lung 51 was removed from the lung 51 and weighed immediately. It was dried by evaporation and weighed again to obtain the wet-to-dry lung weight ratio for each dog. The prepared heart-lung assembly was then suspended from a load cell inside a humidified, isothermal box.

The lungs 51 were connected to the circulation system as shown in FIG. 11, and all air bubbles were removed from the system. The lung weight and arterial, venous and airway pressures were recorded on a strip chart recorder for the duration of the experiments. The blood reservoir 59 was a double-jacketed flask with warm water circulating through the outer chamber to maintain a constant perfusate temperature. A second flask of the same construction was filled with water and was used as a bath 57 for the osmotic injectate solution to be maintained within one degree of the circulating blood. A mercury thermometer (not shown) was used to measure the temperature of the blood and the injectate bath 57. A section of bypass tubing 61 was placed in parallel with the flow through the lung 51.

Before the lungs 51 were extricated, the blood was allowed to circulate through the bypass system. During this time, a series of hypertonic and normal saline injections of different volumes were made, and their signals were recorded with the USV/Z probe 10. These injections consisted of 1, 2, and 3 ml boluses of normal saline and the same regimen of hypertonic (6%) saline. The osmotic solution was mixed from sterile normal saline solution and laboratory grade salt. This saline solution had the same USV signal as pure blood. The bypass curves recorded served as input data for the mathematical model. After the lungs were hung and perfused, the first baseline Radioisotope Multiple Indicator Dilution (RMID) and osmotic curves were obtained. The osmotic injections consisting of one 3 ml bolus of normal saline and one 3 mL bolus of hypertonic saline were administered immediately following the RMID injections. The RMID/osmotic regimen was repeated after a one hour baseline interval. This hiatus was designed to help confirm the integrity of the lung microvascular barrier (LMB) during baseline and to ensure that the first osmotic bolus had not adversely affected the lung. The lung was then injured with an injection of 0.5 ml oleic acid mixed with 3 ml of blood. When it was determined that injury had occurred, the final RMID/osmotic curves were obtained.

Figure 9:
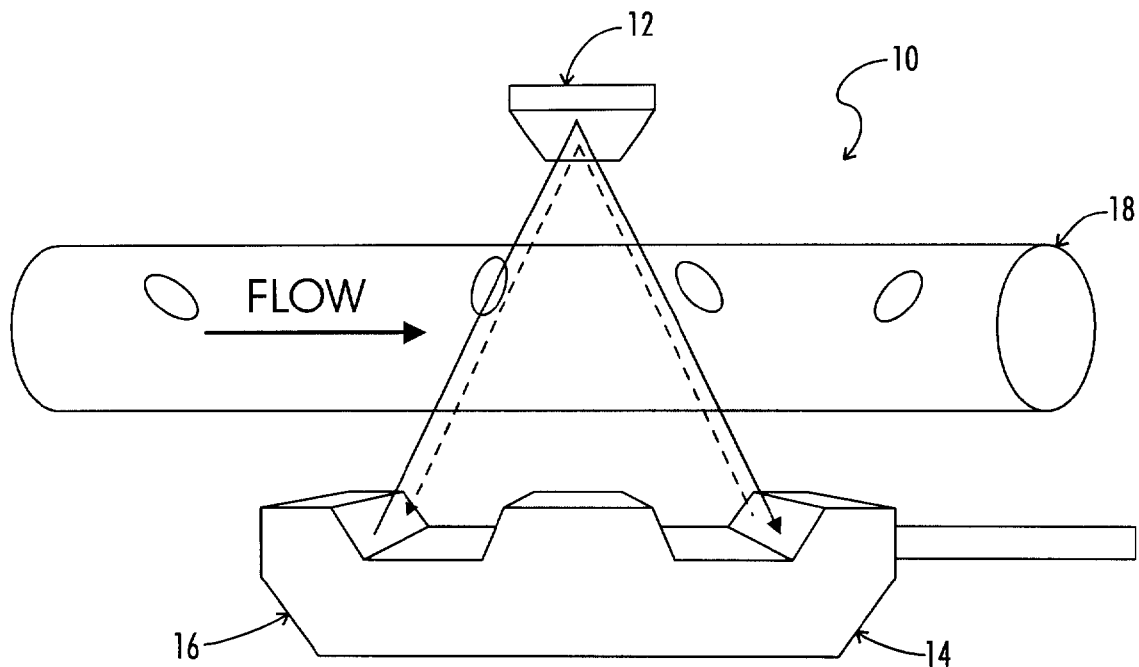
FIG. 9 is a schematic diagram of conventional ultrasonic velocity and impedance probe having a pair of transducers and an acoustic reflector for measuring the ultrasonic velocity and electrical impedance of blood flowing through the probe.

The measurements were taken with the USV/Z probe 10, as shown schematically in FIG. 9. The USV/Z probe 10 is an extra-corporeal flow-through device that measures the volumetric flow by detecting the transit time difference between a downstream oriented ultrasound pulse and an upstream pulse. It consists of a probe body which houses two ultrasonic transducers 14 and 16 and a fixed acoustic reflector 12. The transducers 14 and 16 are positioned on one side of the vessel or tube 18 under study and the reflector 12 is positioned midway between the two transducers 14 and 16 on the opposite side of the vessel or tube 18. The electronic ultrasonic circuitry of the flowmeter (not shown) directs a USV/Z probe 10 to measure in both the downstream and upstream directions.

An electrical excitation causes the downstream transducer 14 to emit a plane wave of ultrasound. This ultrasonic wave intersects the vessel or tubing 18 under study in the upstream direction, then bounces off the acoustic reflector 12, again intersects the vessel 18 and is received by the upstream transducer 16 where it is converted into electrical signals. From these signals, the flowmeter then derives an accurate measure of the "transit time" it took for the wave of ultrasound to travel from the downstream transducer 14 to the upstream transducer 16 and back.

Upstream and downstream transit time measurements are made alternately in the flowmeter. This requires a standard against which the individual transit times are measured and memory elements to store relevant transit time information, to allow the upstream-downstream subtraction (sample-and-hold modules). The timing circuitry (not shown) puts a transmit burst on one of the transducers 14 or 16, after which the other transducer 14 or 16 is connected to the receiver. The full flow information is present in the phase of the received signal, so the reception is amplified, clipped, and fed into one of the inputs of a synchronous detector. The other signal detection input is driven with a clipped oscillator signal. Under these operating conditions, the signal detection output is a DC signal linearly proportional to the phase difference between its two inputs. Its value during the whole reception of the burst is averaged in an integrator, and then used to update one of the two sample-and-hold circuits. After a waiting period sufficient to let all acoustic echoes die out, the role of transmitter and receiver is reversed for the opposing transit time measurement; the resulting phase value is stored in the other sample-and-hold. The difference between the two stored values is then the volume flow signal output. The sum of these measurements is the ultrasound velocity signal for indicator dilution measurements. This sequence of measurements is repeated once every millisecond.

The same transmit-receive sequence of the upstream cycle is repeated, but with the transmitting and receiving functions of the transducers 14 and 16 reversed so that the liquid flow under study is bisected by an ultrasonic wave in the downstream direction. Again, the flowmeter derives from this transmit-receive sequence an accurate measure of transit time.

It is important to note that the transit time of ultrasound passing through a vessel/conduit 18 is affected by the motion of liquid flowing through that vessel 18. During the upstream cycle, the sound wave travels against flow and the total transit time is increased by a flow dependent amount. During the downstream cycle, the sound wave travels with flow and total transit time is decreased by the same flow-dependent amount. The flowmeter subtracts the downstream transit time from the upstream transit time utilizing wide-beam ultrasonic illumination. This difference of integrated transit times is a measure of volume flow rather than velocity.

During operation of the probe 10, one ray of the ultrasonic beam undergoes a phase shift in transit time proportional to the average velocity of the liquid times the path length over which this velocity is encountered. With wide-beam ultrasonic illumination, the receiving transducer sums (integrates) these velocity-chord products over the full width of the vessel 18 and yields volume flow; average velocity times the cross sectional area of the vessel 18. Since the transit time is sampled at all points across the vessel diameter, volume flow measurement is independent of the flow velocity profile. Ultrasonic beam rays which cross the acoustic window without intersecting the vessel 18 do not contribute to the volume flow integral. Volume flow is therefore sensed by perivascular probes even when the vessel 18 is smaller than the acoustic window. This is the traditional use of the ultrasonic device as a flowmeter. However, this method implements a different function for osmotic measurements.

The signal from this sensor is influenced by the velocity of sound in blood. When blood is diluted by saline solution with the same sonic velocity as normal physiological fluid, the alteration in the signal is primarily the dilution of plasma proteins. Thus, the flowmeter signal can be directly altered to be a reading of protein concentration.

The USV/Z probe 10 can be altered for measuring impedance by simply using conductive tubing (not shown) for the inlet and outlet connectors, and placing this as one arm of an AC Wheatstone bridge. Then, variations in the electrical conductance of the solution in the probe 10 are sensed as an impedance change.

Figure 10:
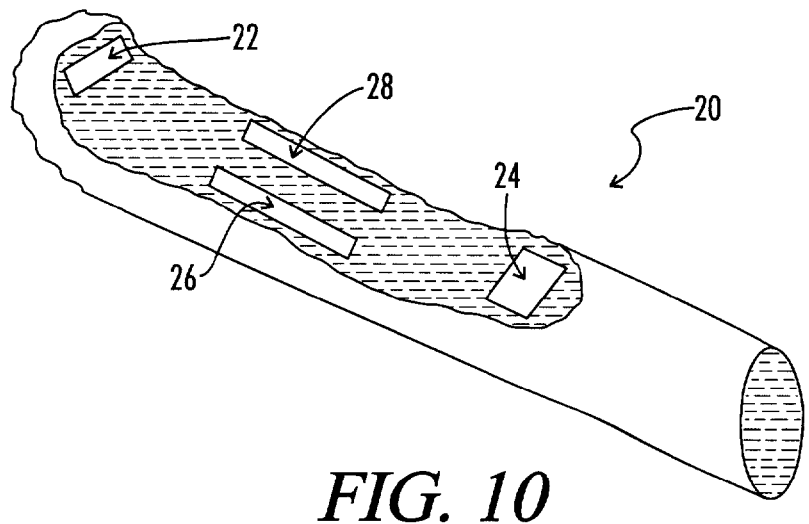
FIG. 10 is a schematic diagram of a catheter tip device having two sound crystals for measuring ultrasonic velocity and two electrodes for measuring electrical impedance of the blood.

In a second embodiment, the sound velocity and impedance transducers can be implemented in a catheter tip system 20 (as shown in FIG. 10). This device provides ultrasound and impedance measurements in the vicinity of the blood passing the tip. The catheter 20 used typically has a temperature sensor (not shown) for measuring blood temperature and two sound crystals 22 and 24 for determining the velocity of ultrasonic waves in the blood flowing past the catheter 20, as well as two electrodes 28 and 26 for determining the impedance of the blood. The angular placement of the two sound crystals 22 and 24 is such that a reflector will not be needed. The catheter 20 will not measure volumetric flow itself.

The salt and protein concentrations in the capillary, and water exchange between the capillary and interstitium were modeled with five nonlinear differential equations. While salt in concentrations above normal has a small PS for capillary escape, we were unable to detect significant NaCl exchange across the LMB from the impedance curves. Therefore, we assumed that hypertonic saline passed through the lung essentially as an intravascular indicator in both normal and injured lungs. Thus, $$\frac{\partial C_S}{\partial t} + \frac{F}{V_C(t)} \frac{\partial C_S}{\partial x'} = 0 \tag{1}$$

where, x' is the position along the capillary normalized to capillary length, $C_S$ is concentration of NaCl in the plasma, F is blood plasma flow and $V_C$ is allowed to change with time due to influx of fluid from the interstitium. The blood protein concentration is reduced due to dilution by exchanging fluid drawn by the hypertonic saline from the interstitium as follows $$\frac{\partial C_P}{\partial t} + \frac{F}{V_C(t)} \frac{\partial C_P}{\partial x'} = -\frac{K(t)C_P(t)}{V_C(t)}(C_S(t) - C_{SI}(t)) \tag{2}$$

K(t) is a parameter that includes capillary filtration and reflection coefficients defined below. Since protein moves very slowly through the paraendothelial clefts, protein transport terms have been neglected in the RHS of Equation 2. Interstitial concentration of salt changes due to water efflux from the interstitium according to the equation $$\frac{\partial C_{SI}}{\partial t} = \frac{K(t)C_{SI}(t)}{V_I(t)}(C_S(t) - C_{SI}(t)) \tag{3}$$

The interstitial and capillary volumes will alter as fluid shifts in response to the osmotic transient in the following manner $$\frac{\partial V_I}{\partial t} = -K(t)(C_S(t) - C_{SI}(t)) \tag{4}$$

$$\frac{\partial V_C}{\partial t} = K(t)(C_S(t) - C_{SI}(t)) \tag{5}$$

The parameter K(t) involves the product of the capillary filtration coefficient for $H_2O$, capillary surface area, the reflection coefficient and other quantities. Since capillary surface area varies as the square root of capillary volume, K(t) is expressed as follows $$K(t) = \Psi_O \sqrt{V_C(t)} \tag{6}$$

where, K(t) has units of $ml^2/s \cdot g$, and cylindrical geometry is assumed for the capillary.
$\Psi_o$ is a constant defined as $$\Psi_0 = \frac{2\sqrt{\pi l_C} L_C \sigma_S RT}{\mu_S} \tag{7}$$

and,
$L_C$=$H_2O$ Filtration coefficient of the capillary endothelium per unit area $(ml/s \cdot cm^2 \cdot mm\ Hg)$[1].

[1] The filtration and reflection coefficients are the averages of the coefficients for the capillary endothelial cells and the gap junctions.

$l_C$=Capillary length (cm).
$s_S$=NaCl reflection coefficient of the capillary endothelium.
$\mu_S$=Molecular weight of NaCl (g/mol).
R=Gas constant $(19.3 \times 10^6\ mm\ Hg \cdot ml/mol \cdot °K)$.
T=Temperature (°K).

The initial and boundary conditions for Equations 1–7 are

| $C_P(x, 0) = C_{PB}$ | $C_P(0, t) = C_{Pin}$ |
|---|---|
| $C_S(x, 0) = C_{SB}$ | $C_S(0, t) = C_{Sin}$ |
| $C_{SI}(x, 0) = C_{SB}$ | $V_C(0) = V_{CO}$ |
|  | $V_I(0) = V_{IO}$ |

$$K(0) = K_O = \Psi_O \sqrt{V_{CO}}.$$

$C_{SB}$ and $C_{PB}$ are the measured baseline concentrations of NaCl and protein in the blood. $C_{Sin}$ and $C_{Pin}$ are the salt and protein concentration input curves to the capillary. The time delay between injection and appearance of the indicator ($t_{tot}$) was divided evenly between the arterial and capillary compartments, and the capillary portion of $t_{tot}$ was multiplied by blood plasma flow to obtain $V_{CO}$, $K_O$ and $V_{IO}$ are regression parameters of the model.

We made substitutions for $C_P$ and $C_S$ to recast the model in terms of the measured variables $\Delta USV$ and $\Delta \kappa$. We assumed $\Delta USV$ during a bolus was linearly related to the change in protein concentration and change in salt concentration in the blood, and that $\Delta \kappa$ was linearly related to the change in salt concentration as follows:

$$\Delta USV = A_1 \cdot (C_P - C_{PB}) + A_2 \cdot (C_S - C_{SB}) \tag{8}$$

$$\Delta \kappa = B \cdot (C_S - C_{SB}) \tag{9}$$

where $C_S$ and $C_P$ are the blood saline and protein concentrations during the osmotic bolus. The coefficients $A_1$, $A_2$, and B were determined from normal and 6% saline calibration injections made through the bypass before the lungs were perfused.

The assumption that $\Delta \kappa$ is dependent only on the change in salt concentration is reasonable when one considers that the electrical conductance of the blood/bolus mixture is dominated by the increased salt concentration, and that the effects of erythrocyte volume changes due to shrinking and dilution are negligible. These substitutions altered Equations 1 and 2 as shown below:

$$\frac{\partial (\Delta \kappa)}{\partial t} + \frac{F}{V_C(t)} \frac{\partial (\Delta \kappa)}{\partial x'} = 0 \tag{10}$$

$$\frac{\partial (\Delta USV)}{\partial t} + \frac{F}{V_C(t)} \frac{\partial (\Delta USV)}{\partial x'} = \tag{11}$$

$$\frac{A_2}{B} \frac{\partial (\Delta \kappa)}{\partial t} - \frac{F}{V_C(t)} \left[ \frac{\partial (\Delta USV)}{\partial x'} - \frac{A_2}{B} \frac{\partial (\Delta \kappa)}{\partial x'} \right] +$$

$$\frac{K(\Delta USV - (A_2/B)\Delta \kappa + A \cdot C_{PB})}{V_C(t)} \cdot \left[ \frac{\Delta \kappa}{B} + C_{SB} - C_{SI} \right]$$

where $\Delta USV$ and $\Delta \kappa$ are functions of time and capillary length with initial and boundary conditions:

$\Delta USV(x, 0) = 0$  $\Delta USV(0, t) = 0$ $\Delta\kappa(x, 0)=0$  $\Delta\kappa(0, t)=\Delta\kappa_{bp}$ Equations 10 and 11 along with Equations 3–6 constitute the final homogeneous capillary equations. The conductance input curve for the homogeneous model was $\Delta\kappa_{bp}$, and the USV input curve was zero. The null boundary condition for $\Delta$USV is appropriate only if the saline bolus is at a concentration of 6%.

During the experiment, the arterial and venous pressures were monitored continuously and adjusted before each set of indicator curves to maintain certain conditions. Flow was calibrated at the beginning of each protocol and monitored throughout the remainder of the experiment. The dog body mass was obtained immediately following anesthetization. The wet lung weight (WLW) is the pre-injury weight of the portion of the lung 51 that was used in the study. It is calculated as follows:

$$WLW = D_{post} \times \frac{W_{pre} - D_{pre}}{D_{pre}} + D_{pre} \qquad (22)$$

where, $D_{post}$ is the post-mortem dry lung weight; $W_{pre}$ is the pre-injury wet lung weight, and $D_{pre}$ is the pre-injury dry lung weight including blood. Hematocrit was determined by measuring the packed cell volume in a centrifuged blood sample. Total protein was measured by refractometry, and the plasma sodium chloride concentration was determined by flame photometry.

After testing, statistics indicated a significant increase in EVLW and wet-to-dry ratios after oleic acid injury. It was further determined that $\sigma K$ is the osmotic conductance normalized to WLW. It is related to the constant K that appears in the following equation:

$$\sigma K = K_{model} \times [(2.9 \times 10^{-5}(g_{NaCl}/\text{ml})/(mOsm_{NaCl}/l)] [3600 \text{ sec/hour}][l/WLW] \qquad (23)$$

There was a significant decrease in $\sigma K$ with oleic acid injury. It should be further noted that the interstitial volume measured by the osmotic technique showed significant changes with injury, but the interstitial volume measured by RMID did not.

Figure 2:
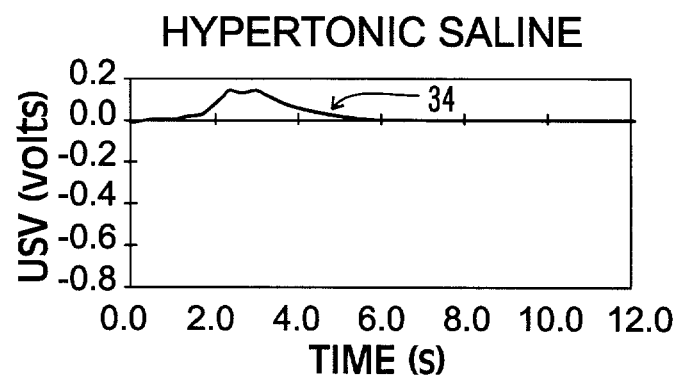
FIG. 2 is a graph of ultrasonic velocity versus time for flowing blood with a hypertonic saline added.
Figure 4:
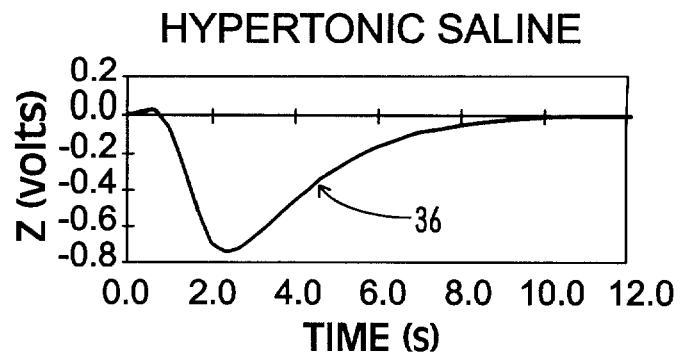
FIG. 4 is a graph of impedance versus time for flowing blood with a hypertonic saline added.
Figure 5:
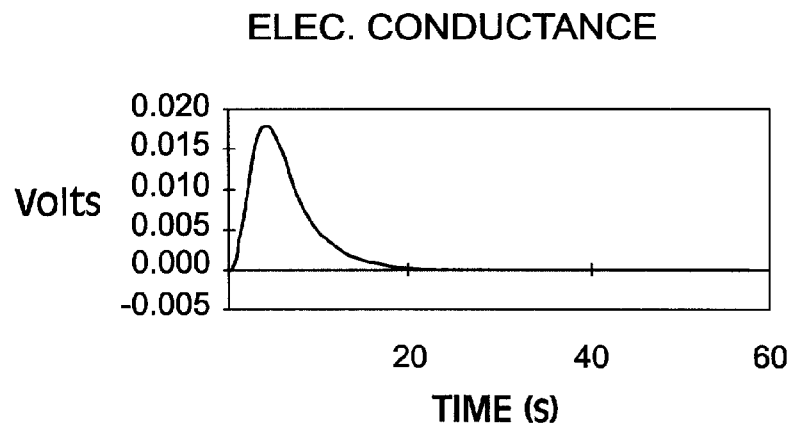
FIG. 5 is a graph of the pre-injury saline conductance curve from a hypertonic bolus injected into the lung.
Figure 6:
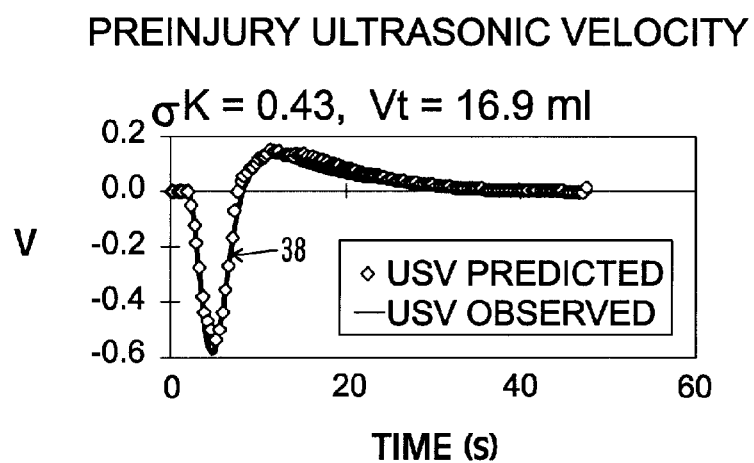
FIG. 6 is a graph of the pre-injury saline ultrasonic velocity curve from hypertonic bolus injected into the lung.
Figure 7:
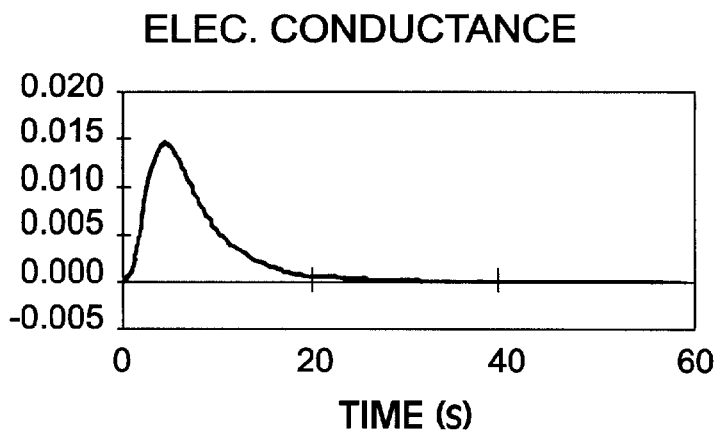
FIG. 7 is a graph of the post-injury saline conductance curve from a hypertonic bolus injected into the lung.
Figure 8:
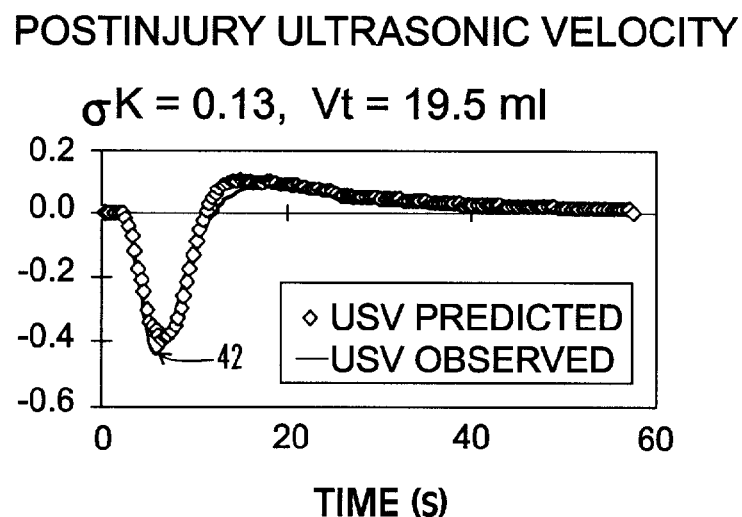
FIG. 8 is a graph of the post-injury saline ultrasonic velocity curve from hypertonic bolus injected into the lung.

Each test provided three sets of RMID curves, three osmotic USV curves, and three impedance dilution curves. Each RMID set contained four curves: RBC, albumin, water, and urea or butanediol. FIGS. 2 and 4 are typical $\Delta$USV(t) and $\Delta$Z(t) data obtained from a bolus of 6% saline through the bypass circulation. Often a signal disturbance is detected when the bolus passes through the probe 10, but the average signal change is always very close to zero, as illustrated by FIG. 2. Representative pre-injury and post-injury $\Delta$USV(t) curves are shown in FIGS. 6 and 8, and the corresponding conductance curves are shown with the $\Delta K(t)$ in FIGS. 5 and 7.

The osmotic potency of the hidden indicator is considerable, and its passage through the capillary bed draws water from the surrounding interstitium by osmosis. This water influx dilutes the blood/saline mix and is observed as a decrease in the USV signal. The interstitial osmolarity is increased by the dehydration effects of the hypertonic saline, and when the indicator bolus passes from the lung, the hyper-osmotic interstitium draws water from the isotonic blood that follows. This increases the protein concentration in the capillary, and is observed as an increase in the USV signal. The final USV signal is a sharp decrease from baseline (salt and protein dilution) followed by a more disperse increase from baseline (protein concentration).

Figure 3:
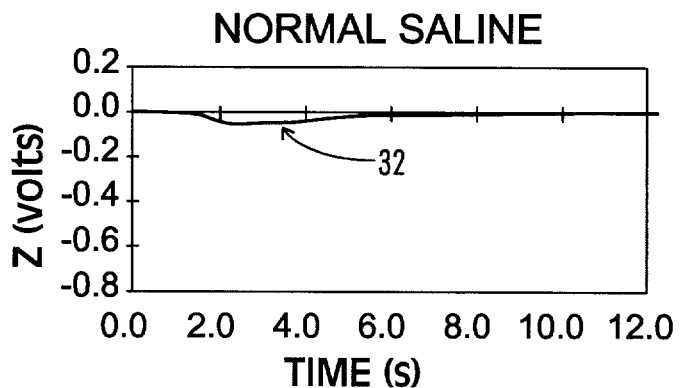
FIG. 3 is a graph of impedance versus time for flowing blood with a normal saline added.

It was determined that injection of normal and hypertonic saline (6%) into blood flowing through the ultrasonic velocity-impedance probe 10 gave quite different indicator curves. A set of such curves is given in FIGS. 1–4. The ultrasonic velocity (USV) curve for normal saline 30 injected into flowing dog blood gave a typical indicator dilution curve when the ultrasonic velocity is measured (as shown in FIG. 1). This measurement essentially senses the dilution of normal serum protein by the normal saline. This same bolus produces a small change in the impedance curve of the normal saline 32 (shown in FIG. 3) because the only alteration in electrical impedance is that due to dilution of the baseline hematocrit and proteins. Salt content is not altered from baseline. Similarly, if 6% saline is injected into the blood stream, very little signal results because the USV in 6% saline is virtually identical to that of whole blood. Thus, the hypertonic bolus is "hidden" from the USV detector 10, and the signal from the bolus cannot be differentiated from the baseline blood signal. The USV curve for hypertonic saline 34 shows only a slight alteration from baseline caused by hypertonic saline (as seen in FIG. 2). If the saline concentration had been lowered slightly, no curve would have been seen. Conversely, the impedance (Z) curve for hypertonic saline 36 (shown in FIG. 4) shows a significant alteration from baseline which is virtually identical in shape to the normal saline indicator USV curve 30. When these bolus injections are allowed to flow through a lung capillary bed, significantly different results are seen.

After passage through the lung, the normal saline USV curve 30 and hypertonic impedance curve 36 are virtually identical (except for different calibration factors which alter the amplitude). This suggests that even hypertonic saline undergoes little transcapillary exchange during a single pass through the lungs. The pre-injury USV curve 38 with simulation outputs is very different however, as is shown in FIG. 6. This curve 38 shows a negative peak followed by a positive peak. This is consistent with an osmotic exchange of water from the extravascular space to the intravascular space, and subsequent return. The initial negative hump in the osmotic curve 38 is due to water movement from the interstitium to the capillary in response to the osmotic gradient. The point when the curve crosses the baseline is the point of osmotic equilibrium ($t_{eq}$) between the interstitium and the capillary. From this point forward, the osmotic gradient is reversed and water movement is from the capillary into the interstitium. Assuming no solute movement across the LMB, the interstitium must gain exactly as much water during the second half of the curve as it loses during the first half to restore osmotic equilibrium to the blood. This implies that the area of the negative and positive lobes should be equal. It should be noted that this USV measurement probably measures only exchanged water, since the hypertonic bolus causes little effect on the USV curve 34, as is shown in FIG. 2. Thus, ultrasonic velocity is a very selective method for measuring extracted water.

This forms the basis upon which $\sigma K$ can be determined from the hypertonic bolus curve in FIG. 6. As discussed earlier, a mathematical model was derived for the change of protein and saline concentrations in the lung capillaries as a hypertonic bolus passes through the lung.

Fitting the model to the data of FIG. 6 (shown as a solid line) produced $\sigma K$ and the volume of the extravascular space. FIG. 8 shows how the USV curve 42 changes after oleic acid injury. The first peak is flattened suggesting that the injured endothelium cannot maintain the same quality of osmotic separation as the normal capillary. FIGS. 5 and 7 are graphs of the electrical conductance of the lungs in the pre-injury and post-injury state.

When the pre-injury and post-injury osmotic curves are plotted on the same scale, it is easy to see the effect of an oleic acid injury on the shape of the curve. When the lung is injured, $t_{eq}$ is delayed, and the negative lobe is not as sharp. Also, the entire post-injury curve is longer in duration than the pre-injury curve. These changes in the $\Delta USV(t)$ curve with injury were characteristic across all studies, due mainly to increased permeability associated with oleic acid injury of the lungs 51. Also, analysis of the two baseline osmotic measurements showed no significant changes in K, or $V_{IO}$. The coefficients of variation for the osmotic model are higher than those for the RMID SS model.

Experiments were conducted on the lungs of five dogs. After the mathematical model was constructed to account for flow heterogeneity in the lung, it was found that $\sigma K$ (normalized to wet lung weight) decreased significantly from 0.16±0.03 ml/[hr-(mosm/l)-g wet lung wet] at baseline to 0.07±0.07 after oleic injury (P<0.05). The ability of the model to fit the data is shown by the solid lines in FIGS. 6 and 8. This significant decrease in $\sigma K$ corresponded to other measures of capillary damage. Extravascular lung water (EVLW) measured by indicator dilution of $^3HOH$ increased from 1.27±0.14 ml per gram blood free dry lung weight to 3.76±0.42, a significant increase in pulmonary edema. Post-mortem wet-to-dry weight ratios of lung went from 2.96±0.33 to 8.84±1.13, also a significant increase (P<0.05). Radioisotope indicator dilution studies showed an increase in the ratio of capillary PS for $^{14}C$-urea to that for $^{14}C$-butanediol consistent with increases in permeability. However, these values did not reach statistical significance. This number went from 0.71±0.07 to 0.98±0.11 (P<0.05). The volume ($V_{IO}$) resulting from the osmotic data curve fit increased significantly from 18.27 to 31.94 ml. This volume approximated the interstitial volume of distribution for $^{14}C$-butanediol. Thus the change in $\sigma K$ corresponds to other measures of acute lung injury and has a relatively higher sensitivity. The quantity decreases because the lung injury causes the reflection coefficient ($\sigma$) to approach 0 (no osmotic barrier between the blood and the extravascular space) more rapidly than the injury is increasing filtration coefficient (K). Baseline changes in protein or salt content will not affect the measurement because it depends on the change of USV from baseline, not the absolute value of baseline proteins. Thus, the method is feasible and capable of measuring acute lung injury, and it is furthermore shown that a significant decrease in the measurement of $\sigma K$, as discussed above, allows for determination of lung injury.

A second embodiment of the system uses a catheter tip sensor assembly 20 as shown in FIG. 9.

From analyzing the results of the methods presented above, it is clear to see how the ultrasonic velocity and impedance method can be used to determine lung vascular injury in human patients as an alternative to radioisotope multiple indicator dilution. The method begins by either inserting a catheter tip sensor 20 (FIG. 10) into the patient's blood circulatory system or clamping an extracorporeal sensor assembly (FIG. 9) in an arterial catheter shunting a portion of the vascular system downstream of the lung. A bolus of hypertonic saline is then injected into the blood circulatory system upstream of the lung (jugular vein) and allowed to flow through the lung toward the sensors. Simultaneous measurements are then taken of the ultrasonic velocity and electrical impedance of the blood, as the combined blood and saline pass the sensors. These measurements are then analyzed using the mathematical analysis discussed above, whereby lung vascular injury can be detected by comparing the observed data with the parameters from studies of healthy lungs. Finding a significant decrease in the measured capillary transport quantity ($\sigma K$) from the predetermined capillary transport quantity for a healthy lung is a significant indicator of lung vascular injury.

Thus, although there have been described particular embodiments of the present invention of a new and useful System and Method for Measurement of Lung Vascular Injury by Ultrasonic Velocity and Blood Impedance, it is not intended that such references be construed as limitations upon the scope of this invention except as set forth in the following claims.

What is claimed is:

1. A method of measuring microvascular injury to a lung in a patient comprising the steps of:

a) positioning a sound velocity sensor and an impedance measurement sensor whereby a sound velocity and an impedance in blood flowing through the patient's lung at a predetermined location in the patient's vascular system can be simultaneously measured;

b) introducing a quantity of an osmotic indicator material into blood entering the lung so that a portion of the indicator material passes with the blood through a bed of capillaries in the lung before leaving the lung;

c) simultaneously obtaining at least one sound velocity measurement and one impedance measurement of the blood as it passes the sound velocity and impedance sensors with the indicator material in the blood;

d) deriving at least one post-injection capillary transport factor from the sound velocity and impedance measurements, the post-injection capillary transport factor including the product of at least one capillary reflection coefficient and at least one capillary filtration coefficient corresponding to the capillaries in the lung; and e) comparing the post-injection capillary transport factor to a pre-injection capillary transport factor corresponding to capillaries in a non-injured lung.

2. The method of claim 1 wherein the osmotic indicator material comprises a hypertonic fluid.

3. The method of claim 2 wherein the hypertonic fluid comprises hypertonic saline.

4. The method of claim 3 wherein multiple sound velocity and impedance measurements are obtained during a period of time after the hypertonic saline is introduced into the blood to provide an observed sound velocity curve and an observed impedance curve, and wherein the step of comparing the post-injection capillary transport factor to the pre-injection capillary transport factor includes comparing the observed sound velocity curve to a predicted sound velocity curve.

5. A method of measuring injury to the blood capillaries in the lungs of a patient comprising the steps of:

a. coupling a sound velocity sensor and a blood impedance sensor to a portion of the patient's vascular system downstream of the lung;

b. injecting a pre-determined volume of saline into the vascular system upstream of the lung;

c. taking a series of post-injection sound velocity and blood impedance measurements over a period of time corresponding to passage of blood combined with at least some of the saline through the lung and proximate the sound velocity and blood impedance sensors; and d. comparing the post-injection sound velocity and blood impedance measurements to pre-determined sound velocity and blood impedance measurements corresponding to a non-injured lung.

6. The method of claim 5 wherein the sound velocity sensor and the blood impedance sensor are mounted together to a catheter tip that is attachable to a catheter and wherein the step of coupling the sound velocity and blood impedance sensors to the vascular system includes introducing the catheter into the vascular system so that the blood will pass the catheter tip.

* * * * *

UNITED STATES PATENT AND TRADEMARK OFFICE
CERTIFICATE OF CORRECTION

PATENT NO.  : 5,935,066
DATED       : August 10, 1999
INVENTOR(S) : Thomas R. Harris It is certified that error appears in the above-identified patent and that said Letters Patent is hereby corrected as shown below:

Column 1, line 5, should read

--This invention was made with governement support under HL07123 and HL39155 awarded by the National Institutes of Health --.

Signed and Sealed this

Twenty-sixth Day of September, 2000

Attest:

Q. TODD DICKINSON

*Attesting Officer*   *Director of Patents and Trademarks*